(12) United States Patent
Lau

(10) Patent No.: US 8,357,282 B2
(45) Date of Patent: Jan. 22, 2013

(54) OPTOELECTRONIC SEPARATION OF BIOMOLECULES

(75) Inventor: Aldrich N. K. Lau, Palo Alto, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 414 days.

(21) Appl. No.: 12/623,201

(22) Filed: Nov. 20, 2009

(65) Prior Publication Data
US 2010/0133105 A1 Jun. 3, 2010

Related U.S. Application Data

(63) Continuation of application No. 11/426,222, filed on Jun. 23, 2006, now abandoned.

(60) Provisional application No. 60/731,123, filed on Oct. 27, 2005.

(51) Int. Cl.
*B03C 5/02* (2006.01)

(52) U.S. Cl. ........ 204/643; 427/457; 430/35; 204/155

(58) Field of Classification Search ............... None
See application file for complete search history.

(56) References Cited

U.S. PATENT DOCUMENTS

| | | |
|---|---|---|
| 4,545,677 A | 10/1985 | Chupp |
| 4,655,885 A | 4/1987 | Hill et al. |
| 4,661,913 A | 4/1987 | Wu et al. |
| 4,756,427 A | 7/1988 | Gohde et al. |
| 4,859,582 A | 8/1989 | Stryer et al. |
| 5,007,732 A | 4/1991 | Ohki et al. |
| 5,888,370 A | 3/1999 | Becker et al. |
| 5,903,296 A | 5/1999 | Shimizu et al. |
| 5,993,692 A | 11/1999 | Tarumi et al. |
| 6,287,832 B1 | 9/2001 | Becker et al. |
| 6,641,708 B1 | 11/2003 | Becker et al. |
| 6,723,299 B1 | 4/2004 | Chen et al. |
| 6,749,736 B1 | 6/2004 | Fuhr et al. |
| 6,790,330 B2 | 9/2004 | Gascoyne et al. |
| 6,797,524 B1 | 9/2004 | Seul |
| 2001/0007775 A1* | 7/2001 | Seul et al. ............... 436/534 |
| 2001/0021534 A1* | 9/2001 | Wohlstadter et al. ........ 436/518 |
| 2002/0028198 A1* | 3/2002 | Nishi et al. ............... 424/94.61 |
| 2002/0160470 A1 | 10/2002 | Zhang |
| 2003/0159999 A1 | 8/2003 | Oakey et al. |
| 2003/0224528 A1 | 12/2003 | Chiou et al. |
| 2005/0006238 A1 | 1/2005 | Jaffe et al. |
| 2005/0009101 A1 | 1/2005 | Blackburn et al. |
| 2005/0142032 A1 | 6/2005 | Hoenes et al. |
| 2005/0164372 A1 | 7/2005 | Kibar |
| 2005/0175981 A1 | 8/2005 | Voidman et al. |
| 2005/0184008 A1 | 8/2005 | Schacht et al. |
| 2005/0207940 A1 | 9/2005 | Butler et al. |
| 2005/0221333 A1* | 10/2005 | Sundararajan et al. ........ 435/6 |

(Continued)

FOREIGN PATENT DOCUMENTS

| | | |
|---|---|---|
| WO | WO9641154 | 12/1996 |
| WO | WO2005100541 | 10/2005 |

OTHER PUBLICATIONS

Chiou et al., Cell addressing and trapping using novel optoelectronic tweezers, Jan. 2004, IEEE Int Conf on Micro Electro Mechanical Systems, pp. 21-24.*

(Continued)

*Primary Examiner* — N. C. Yang

(57) ABSTRACT

The present teachings relate to systems and methods for separation of substances such as cells, nucleic acids, and carbon nanotubes. The substances are combined with a separation medium in a liquid sample cavity, for example a microchannel, and transit through the separation by optically activated dielectrophoretic forces. The substances are advantageously labeled and visualized using a microscope and camera.

55 Claims, 3 Drawing Sheets

U.S. PATENT DOCUMENTS

2006/0091015 A1    5/2006    Lau
2010/0133105 A1    6/2010    Lau

OTHER PUBLICATIONS

EP06849794.0 Extended European Search Report dated May 2, 2011.

PCT/US06/24652 International Search Report and Written Optinion dated Oct. 23, 2008.

Arai et al., Tying a Molecular Knot with Optical Tweezers, Nature, Jun. 1999, vol. 399, 446-448.

Arnold et al., Dielectric measurements on electro-manipulation media, Biochem. Biopys., 1993, vol. 1157, 32-44.

Arnold, Positioning and Levitation Media for the Separation of Biological Cells, IEEE Transactions on Industry App., 2001, vol. 37 (5), 1468-1475.

Ashkin et al., Optical Trapping and Manipulation of Single Cells Using Infrared Laser Beams Nature, Dec. 1987, vol. 330, 769-771.

Brochure for BD FACSCantoTM Flow Cytometer, BD Biosciences, Apr. 2004.

Carter et al., Endocrine-Related Cancer, 2004, vol. 11, 659-87.

Chapman, Instrumentation for flow cytometry, Journal of Immunological Methods, 2000, vol. 243, 3-12.

Chiou, et al., "Cell addressing and trapping using novel optoelectronic tweezers", IEEE Int Conference on Micro Electro Mechanical Systems, Jan. 2004, 21-24.

Chiou et al., Massively Parallel Manipulation of Single Cells and Microparticles Using Optical Images, Nature, Nature Publishing Group, Jul. 2005, vol. 436 (21), 370-372.

Chiou et al., Light actuation of liquid by optoelectrowetting, Sensors and Actuators A, 2003, 104, 222-228.

Das et al., Dielectrophoretic Segregation of Different Human Cell Types on Microscope Slides, Anal. Chem., May 2005, vol. 77 (9), 2708-2719.

Engineers create optoelectronic tweezers to round up cells, microparticles, Sep. 19, 2005.

Forster et al., Use of moving optical gradient fields for analysis of apoptotic cellular responses in a chronic myeloid leukemia cell model, Analytical Biochemistry, 2004 vol. 327, 14-22.

Fu et al., A microfabricated fluorescence-activated cell sorter, Nature Biotechnology, Nov. 1999, vol. 17, 1109-1111.

Green et al., Separation of Submicrometer Particles Using a Combination of Dielectrophoretic and Electrohydrodynamic Forces, J. of Phys. D. : Appl. Phys., 1998, vol. 31, L25-L30.

Hagedorn et al., Traveling-Wave Dielectrophoresis of Microparticles, Electrophoresis, 1992, vol. 13, 49-54.

Horsman et al., Separation of Sperm and Epithelial Cells in a Microfabricated Device: Potential Application to Forensic Analysis of Sexual Assault Evidence, Anal. Chem, 2005, vol. 77 (3), pp. 742-749.

Insulator-based dielectrophoretic particle separator and concentrator—iDEP, Selective Particle Concentrator and Sorter for Biomedical and Homeland Security Applications, Sandia National Laboratories, Fact Sheet, Aug. 2005, SANDI#2005-5329.

Introduction to Antibodies—Flow Cytometry, CHEMICON International, Inc., copyright 1998-2005.

MacDonald et al., Microfluidic sorting in an optical lattice, Nature, 2003, vol. 426, 421-424.

Ohta et al., Manipulation of Live Red and White Blood Cells Via Optoelectronic Tweezers.

Pethig et al., Development of Biofactory-on-a-chip Technology Using Excimer Laser Micromachining, J. of Micromech. And Microeng., 1998, vol. 8, 57-63.

Pohl et al., J. of Appl. Phys., 1958, vol. 29, 1182-88.

Pohl, Herbert A., Dielectrophoresis, The Behavior of Neutral Matter in Nonuniform Electric Fields, Cambridge University Press, 1978, Chapter 15, 350-440.

Rohr et al., Photografting and the Control of Surface Chemistry in Three-Dimensional Porous Polymer Monoliths, Macromolecules, 2003, vol. 36 (5), 1677.1684.

Sakamoto et al., Nippon Sanka Fujinka Gakkai Sasshi, 1990, vol. 44 42 (5), 415-21.

Sandias dielectrophoresis device may revolutionize sample preparation, Sandia National Laboratories, Aug. 2005.

Soo Hoo et al., A Novel Method for Detection of Virus-Infected Cells Through Moving Optical Gradient Fields Using Adenovirus as a Model System, Cytometry, Wiley-Liss, Inc., 2004, Part A 58A, pp. 140-146.

Srinivasan et al. An integrated digital mocrofluidic lab-on-a-chip for clinical diagnostics on human physiological fluids, Lab Chip, The Royal Society of Chemistry, May 4, 2004, pp. 310-315.

Stachowiak et al., Fabrication of Porous Polymer Monoliths Covalently Attached to the Walls of Channels in Plastic Microdevices, Electrophoresis, 2003, vol. 24, 3689-3693.

Stephens et al., The dielectrophoresis enrichment of CD34+ cells from peripheral blood stem cell harvests, Bone Marrow Transplant, Oct. 1996, vol. 18 (4), 777-82.

Stratton et al., Gynecol Oncol., 1984, vol. 17 (2), 185-88.

Talary et al., Electromanipulation and Separation of Cells Using Traveling Electric Fields, J. Phys. D: Appl. Phys., 1996, vol. 29, 2198-2203.

The Fluorescence-Activated Cell Sorter, Sep. 20, 2005.

Wang et al., Cell Separation by Dielectrophoretic Field-flow-fractionation, Anal. Chem, Feb. 2000, vol. 72 (4), 832-39.

Wang et al., Microfluidic sorting of mammalian cells by optical force switching, Nature Biotechnology, Jan. 2005, vol. 23 (1) /83-87.

Yu et al., Towards Stationary Phases for Chromatography on a Microchip: Molded Porous polymer Monoliths Prepared in Capillaries by Photoinitiated in situ polymerization as separation Media for Electrochromatography, Electrophoresis, 2000, vol. 21, 120-127.

\* cited by examiner

FIG. 1
$$\vec{F}_{DEP} = 2\pi\upsilon\varepsilon_m \alpha_r \vec{\nabla}\left(\vec{E}_{RMS}^2\right),$$
$$\alpha_r \equiv Re\left(\frac{\varepsilon_p^* - \varepsilon_m^*}{\varepsilon_p^* + 2\varepsilon_m^*}\right)$$
FIG. 2
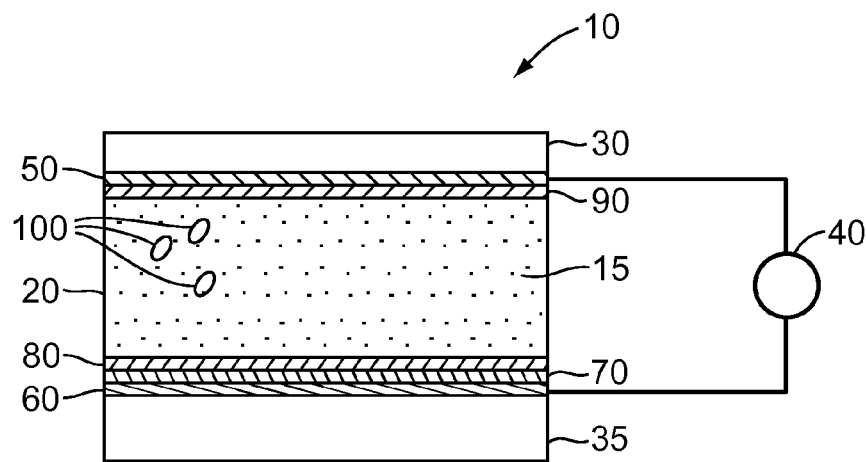
FIG. 3A
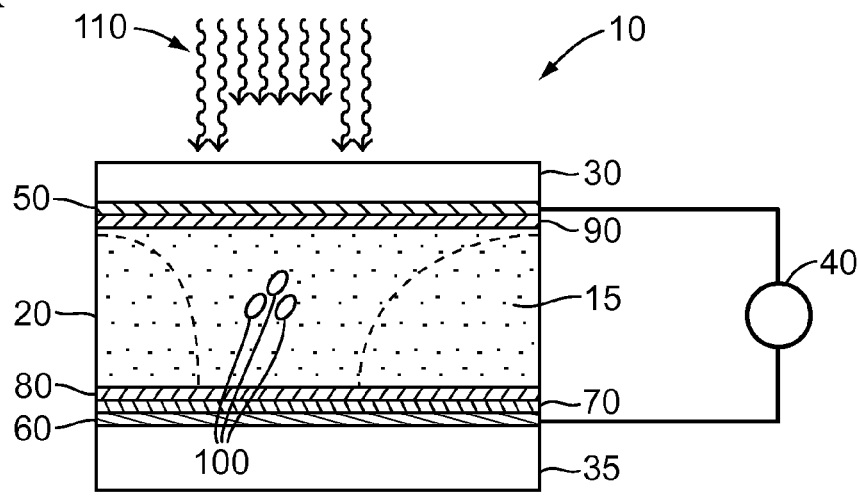

OPTOELECTRONIC SEPARATION OF BIOMOLECULES

CROSS REFERENCE TO RELATED APPLICATIONS

The present application is a continuation of U.S. patent application Ser. No. 11/426,222, filed Jun. 23, 2006, which claims the benefit of U.S. Provisional Patent Application No. 60/731,123, filed Oct. 27, 2005, the contents of each of which are entirely incorporated herein by reference.

FIELD

The present teachings relate to systems and methods for separation of substances such as cells, nucleic acids, and carbon nanotubes.

BACKGROUND

Dielectrophoresis (DEP) is the analog of optical tweezers that are capable of manipulating objects, cells, and even a single molecule in an aqueous solution (P. J. Burke, Nano-dielectrophoresis: Electronic nanotweezers, 2003, Encyclopedia of Nanoscience and Nanotechnology, American Scientific). DEP describes induced particle motion along an electric field gradient due to the interaction of the induced dipole in the particles and the applied electric field (H. A. Phol, Dielectrophoresis, Cambridge University Press 1987). An analytical expression of DEP force is illustrated in FIG. 1 (T. B. Jones, Electromechanics of Particles, Cambridge University Press, 1995), where U is the volume of the object, the factor in parentheses is the RMS value of the electric field, and $\alpha_r$ is the real part of the Clausius-Mosotti factor which relates the dielectric constant of the object $\in_p$ and dielectric constant of the medium $\in_m$. The star (*) denotes that the dielectric constant is a complex quantity.

The term $\alpha_r$ can have any value between 1 and $-\frac{1}{2}$, depending on the applied AC frequency and the dielectric constants of the object and medium. If $\alpha_r$ less than zero, a particle will tend to move towards a lower electric field region. This is commonly referred to as negative DEP. On the other hand, if $\alpha_r$ is positive, a particle will tend to move towards a higher electric field region. This is commonly referred to as positive DEP. DEP force is AC frequency dependent, so by varying the frequency of the applied AC bias, the force can be adjusted from positive to negative DEP, and vice versa. Thus, there are two modes in which DEP forces can operate: positive, in which substances are attracted to high electric field strength regions, and negative, in which substances are repelled by high electric field strength regions.

DEP has been used to manipulate objects (N. G. Green, et al., J. Phys. D., 1997, 30, 2626-2633), to separate viable/non-viable yeast (G. H. Markx, et al., J. Biotechnology, 1994, 32, 29-37) and other micro-organisms such as separating Gram-positive bacteria from Gram-negative bacteria (G. H. Marks, et al., Microbiology, 1994, 140, 585-591), and to remove human leukemia cells and other cancer cells from blood (F. F. Becker, et al., J. Phys. D.: Appl. Phys., 1994, 27, 2659-2662; F. F. Becker, et al., Proc. Nat. Acad. Sci. (USA), 1995, 92, 860-864). The cells are manipulated by a traveling wave generated by a series of patterned electrodes lining up and charged with phase-shifted AC signals (A. D. Goater, et al., J. Phys. D., 1997, 30, L65-L69). The patterned electrodes can be patterned in an independently controlled array to provide such a traveling wave.

Optically activated DEP systems have been compiled using low-power laser light focused to induce DEP between two pattern-less surfaces, such as a indium tin oxide (ITO) transparent glass electrode and a substrate coated with photoconductive material to complete the circuit (P. Y. Chiou, et al., Cell Addressing and Trapping using Novel Optoelectric Tweezers, 2004, IEEE International Conference on Micro Electro Mechanical Systems, Technical Digest, 17$^{th}$ Maastricht, Netherlands, Jan. 25-29, 2004). A non-uniform field is created by a well-defined laser spot, and the objects in the liquid layer in between the two electrodes move towards or away from the illuminated spot by the negative or positive dielectrophoretic force. Silicon nitride coats the photoconductive material to provide separation between the photoconductive material and the liquid layer. Typical light activated DEP relies on a transparent ITO electrode to permit a focused laser beam to pass through the ITO electrode and illuminate a photoconductor.

DEP, whether optically activated or electrically activated can be used to separate or manipulate uncharged objects and objects that have a charge such as DNA, and cells that have a net charge on their surface. Typically, metal electrodes are used in a uniform or non-uniform electric field to provide the driving force to separate or manipulate objects. Electrically activated EP relies on metal electrodes to generate uniform or non-uniform electric fields, providing the driving force to separate or manipulate charged objects. Optically activated EP can rely on a transparent metal or metallic electrode that can permit a light beam, for example, a focused laser, to pass through the electrode and illuminate a photoconductive material adjacent to a non-transparent electrode, generating a non-uniform electric field and providing the driving force to separate or manipulate charged objects.

It can be advantageous to be able to separate objects, including unstable objects like RNA, in a separation medium using a low energy light source. Such separations can be effective and efficient and, in the case of labeled substances, can provide a means for visualization.

SUMMARY

In various embodiments, the present teachings can provide a system for separating substances comprising a liquid sample cavity comprising a first surface and a second surface, a separation medium disposed within said cavity, a transparent electrode positioned proximate to the first surface, a photoconductive material positioned proximate to the second surface, an electrode positioned adjacent the photoconductive material, and an illumination source for illuminating a portion of the photoconductive material with light to provide a region of manipulation between the transparent electrode and the electrode.

In various embodiments, the present teachings can provide process for separating substances in a liquid sample cavity containing a separation medium, wherein the liquid sample cavity comprises a first surface and a second surface, a transparent electrode is positioned proximate to the first surface, a photoconductive material is positioned proximate to the second surface, and an electrode is positioned adjacent to the photoconductive material, said process comprising illuminating a portion of the photoconductive material with light in a manner sufficient to move at least one substance across at least a portion of said separation medium.

In various embodiments, the present teachings can provide process for separating substances comprising (A) contacting a separation medium with said substances to form a composition, (B) disposing said composition in a liquid sample cavity comprising a first surface and a second surface, wherein a transparent electrode is positioned proximate to the first surface, a photoconductive material is positioned proximate to the second surface, and an electrode is positioned adjacent to the photoconductive material, and (C) illuminating a portion of the photoconductive material with light in a manner sufficient to move at least one substance across at least a portion of said separation medium.

In various embodiments, the present teachings can provide a process for separating carbon nanotubes comprising (A) disposing the carbon nanotubes and a liquid separation medium in a liquid sample cavity wherein the liquid sample cavity comprises a first surface and a second surface, a transparent electrode is positioned proximate to the first surface, a photoconductive material is positioned proximate to the second surface, and an electrode is positioned adjacent to the photoconductive material, and (B) illuminating a portion of the photoconductive material with light in a manner sufficient to move at least one carbon nanotube across at least a portion of said separation medium.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings, FIG. 1 illustrates an analytical expression of DEP force.

FIG. 2 illustrates a cross-section of a system for separating substances according to the present teachings.

FIGS. 3A-3C illustrate a process for separating substances using negative DEP force according to the present teachings.

DESCRIPTION OF VARIOUS EMBODIMENTS

Figure 3B:
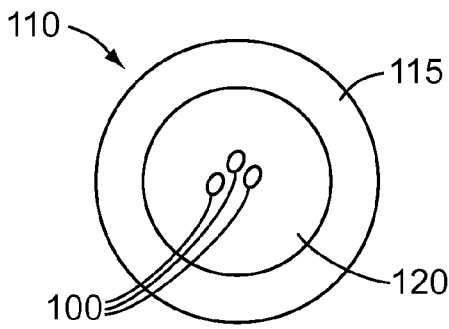

The term "electrode" as used herein refers to the instrumentality used to provide electric current to the region of interest. An example of a metallic electrode is ITO and other compounds in the ITO family. Other metallic electrodes, for example metal oxides are described in M. Saif, et al., Proc. Intl. Conf. Vacuum Web Coating, 10$^{th}$, Fort Lauderdale, Fla., Nov. 10-12, 1996, pp. 286-300; C. G. Granqvist, et al., Appl. Phy. A: Solids and Surfaces, 1993, A57, 19-24; William R. Heineman, et al., Electroanalytical Chem., 1984, 13, 1-113. Examples of metal electrodes include gold, platinum, copper, aluminum, and other metals or alloys known in the electrical arts. Metal electrodes can result in transparent electrodes by sputter, spray, or vapor-deposit to form grids from 100 to 500 mesh of metal (or metals) on a transparent substrate as known in the art (William R. Heineman, et al, Denki Kagaku oyobi Kogyo Butsuri Kagaku, 1982, 50, 142-8). For example, 10 nm Ni/Au can be used as a transparent electrode (Atsushi Motogaito, et al., Physica Status Solidi C: Conf. & Critical Review, 2003, 0(7), 147-150) can also be used. Optically transparent diamond electrodes that exhibit super stability in aggressive solution environments without any micro-structural or morphological degradation can also be used (Greg M. Swain, et al., Abstract of Papers, 225$^{th}$ ACS National Meeting, New Orleans, La., USA, Mar. 23-27, 2003; J. K. Zak, et al., Anal. Chem. 2001, 73 (5), 908-914). In the embodiments where there is optical activation of a photoconductive material through the surface of the electrode, it is desirable to have a transparent electrode. A transparent electrode permits at least a portion of illumination from a light source to reach the photoconductive material, even if the electrode is positioned between the illumination source and the photoconductive material. ITO is an example of a transparent electrode. Gold or platinum can be deposited in a thin layer on a transparent surface, such as glass. The layer of gold or platinum can be thick enough to provide conductivity and sufficiently thin, i.e., thinner than the wavelength of the illumination to permit the illumination to pass through the deposited layer of gold or platinum.

The term "photoconductive material" as used herein refers to a material that has different electrical conductivity properties in a dark state versus an illuminated state. For instance, the photoconductive material can be an insulator in a dark state and a conductor in an illuminated state. Examples of photoconductive materials include amorphous silicon. Other examples include amorphous selenium, polyferrocenylsilane, and other compounds known in the material science arts.

The term "surface modifier" as used herein refers to compounds capable of modifying the surface of an electrode to decrease non-specific adsorption of biomolecules in biological materials. Surface modifier compounds can include any material that can attach to the electrode, semiconductor, spin-on-glass (SOG), or polymer layer and provide hydrophilic characteristics to prevent non-specific adsorption of biomolecules. Examples of such materials include grafting of hydrophilic polymers, i.e. polymers with hydrophilic moieties, for example poly(ethylene glycol) or "PEO" of various molecular weights or polyacrylamides and its copolymers.

The term "illumination source" as used herein refers to any light source providing optical activation to complete the circuit providing a uniform or non-uniform electric field. An example of the illumination source is laser. However, an illumination source can be any light source with accompanying optical components that can provide focus for a beam of light that is on the scale of the biological object to be manipulated. For example, if a cell is the biological object to be manipulated, then the illumination source can provide a focused beam of light on the order of 1.0 to 10.0 microns, or the size of cell to be manipulated. Alternatively, if nucleic acid is the biological object to be manipulated, the illumination source can provide a focused beam of light on the order of 0.1 to 1.0 microns.

The term "power source" as used herein refers to AC or DC power supplies as known in the electrical arts. An AC or DC power supply can provide a uniform or a non-uniform electric field of variable frequency. The AC power supply can have a low frequency bias such that it approaches DC behavior.

In various embodiments, an illumination source can be associated with optical components, a computer, and accompanying software suitable for projecting light patterns. Suitable patterns include, by way of non-limiting example, rings, circles, rectangles, solid dots, solid squares, solid rectangles, and combinations thereof. In various embodiments, at least a portion of the pattern is movable depending on, for example, computer software. In various embodiments, a train of light patterns having various intensities can transverse one end of the separation path to the other. In various embodiments, two trains of light patterns with various intensities can move along the separation path from the same or opposite directions, simultaneously or sequentially, and at the same or different AC frequencies.

The term "glass" and grammatical variations thereof as used herein refer to any glass layer that can be deposited proximate to the electrode, for example between the liquid layer and the photoconductive material. An example of glass that can be deposited is SOG. Commercially available examples of SOG include Accuglass® (Honeywell, Electrical Materials, Sunnyvale, Calif.), which includes T-03AS (thickness 1,040-3,070 Angstroms, dielectric constant at 1 MHz of 6-8, and refractive index at 633 nm of 1.43), P-5S (thickness 925-1,490 Angstroms, dielectric constant at 1 MHz of 4.7, and refractive index at 633 nm of 1.48), and T-12B (thickness 2,100-9,000 Angstroms, dielectric constant at 1 MHz of 3.2, and refractive index at 633 nm of 1.39).

The term "polymer layer" as used herein refers to a material covering a surface uniformly or nonuniformly containing at least one polymer. The term "polymer" refers to material resulting from polymerization. Polymers can include oligomers, homopolymers, and copolymers. Polymerization can be initiated thermally, photochemically, ionically, or by any other means known to those skilled in the art of polymer chemistry. According to various embodiments, the polymerization can be condensation (or step) polymerization, ring-opening polymerization, high energy electron-beam initiated polymerization, free-radical polymerization, including atomic-transfer radical addition (ATRA) polymerization, atomic-transfer radical polymerization (ATRP), reversible addition fragmentation chain transfer (RAFT) polymerization, or any other living free-radical polymerization. In various embodiments, the polymer can be grafted on a surface through unsaturated functionality, for example through (meth)acryloyl and other olefinic functional groups on said surface.

The term "non-specific adsorption of biological material" as used herein refers to indiscriminate adsorption, unintentional adsorption, or undesirable adsorption of biological material of interest to a random location, unknown location, or unwanted location on the electrode or proximate to the electrode.

The term "crosslinked" as used herein refers to attachment of two chains of polymer molecules by bridges, composed of either an element, a group, or a compound, that join certain carbon atoms of the chains by primary chemical bonds. Crosslinking can be accomplished physically, chemically, and covalently.

The term "nucleic acid" as used herein refers to DNA, RNA, and variations of DNA and RNA, such as single strand DNA, double strand DNA, L-DNA, mRNA or iRNA.

The term "liquid sample cavity" as used herein refers to a volume capable of at least partially containing a liquid.

The term "microchannel" as used herein refers to a channel suitable for containing a liquid. The length of the channel can range from about 0.5 to about 10 cm. The inside diameter of the channel can range from about 10 to about 200 μm. According to another embodiment, the inside diameter ranges from about 25 to about 75 μm.

The term "microchip" as used herein refers to a wafer or chip similar in size to a computer chip. The microchip can be a micrototal analysis system (μTAS), or lab-on-a-chip. Such devices are largely fabricated using inorganic substrates such as glass, silica, and quartz, in which a network of channels and other features are obtained using etching processes. The microchip can contain as few as two to as many as thousands of components suitable for manipulating and analyzing substances, such as biological particles, for example cells.

The term "substances" as used herein refers to any material capable of being separated from another substance. In various embodiments, the substances are biological materials such as cells, cell organelles, cell aggregates, tissue, bacteria, protozoa, viruses, proteins, peptides, and nucleic acids. The substances can also be non-biological materials, such as polymers, for example polymer beads. In various embodiments, the polymer beads contain biological materials. The substances can be nanoparticles, for example nanotubes. In various embodiments, the substances are chosen from lipids, polysaccharides, and hydrocarbons, for example terpenes.

In various embodiments, the substances are carbon nanotubes, for example single-wall carbon nanotubes. Single-wall carbon nanotubes can have diameters ranging from about 2 nm, and lengths ranging up to about 100 nm, and can exhibit chirality as prepared. This results in a mixture of semiconducting and metallic forms. It can be desirable to separate the two forms for the purposes of various electronic applications, for example the fabrication of semiconductors.

In various embodiments, the surface chemistry of the substances to be separated, and hence their permeability and $\in_p$, can be selectively altered to provide specified sorting of certain substances. This can be accomplished by coating the surfaces of the substances to be separated. For example, certain substances can be selectively coated with a surface active agent. Such a coating provides discrimination between different types of substances by modulating the permeability (dielectric constant) or surface net charge. Surface active agents can selectively and specifically coat one type of substance but not others. For example, a non-ionic surface-active agent can be used to alter the permeability and/or dielectric constant such that DEP can provide cell sorting for otherwise charged substances. Alternatively, an ionic surface-active agent can be used to alter the permeability and/or dielectric constant such that EP can provide cell sorting for otherwise non-charged cells.

The coating can be accomplished by, for example, physical adsorption, chemi-adsorption, ionic interaction, or by covalent bonding. The coating can be chosen from biological and non-biological materials such as, for example, nucleotides, antibodies (P. Leonard et al., *Enzyme and Microbial Technology* 2003, 32, pp. 3-13), saccharide-functionalized shell crosslinked polymer micelles (M. J. Joralemon et al., *Biomacromolecules* 2004, 5, pp. 903-913), heme compounds, siderophores, and exotoxins (U.S. Patent Application Publication No. US2004/0096910), bateriophages and bacteriophage proteins (U.S. Patent Application Publication No. 2002/0127547), lysozymes (T. Huang et al., *Enzyme and Microbial Technology* 2003, 33, pp. 958-966), biotin, streptavidin, and surface active agents.

The term "surface active agent," or "surfactant," as used herein refers to a material capable of altering the surface tension of a substance. A wide variety of surfactants are known to be available. For example, many are listed with HLB values in McCutcheon's Emulsifiers & Detergents, North American Ed., Manufacturing Confectioner Pub. Co., Glen Rock, N.J., 1988, pp. 1-217. The surfactant can be nonionic or have an anionic charge, cationic charge, or both, e.g., an amphoteric surfactant, where each charge has associated with it a counterion; numerous examples of each are known in the art.

Nonionic surfactants are known in the art and include polyoxyethylene surfactants, e.g., alcohol ethoxylates and alkylphenol ethoxylates; carboxylic acid esters, e.g., glycerol esters and polyoxyethylene esters; anhydrosorbitol esters, e.g., mono-, di- and tri-esters of sorbitan and fatty acids; polyalkylene oxide block copolymers; and poly(oxyethylene-co-oxypropylene) nonionic surfactants. Anionic surfactants are known in the art and include carboxylates, e.g., soaps, polyalkoxycarboxylates and N-acylsarcosinates; sulfonates, e.g., alkylbenzene sulfonates, naphthalene sulfonates and petroleum sulfonates; sulfates, e.g., alcohol sulfates and ethoxylated and sulfated alcohols; and phosphates, e.g., phosphate esters. Cationic surfactants are known in the art and include amines, e.g., aliphatic mono-, di- and polyamines derived from fatty and rosin acids; and quaternary ammonium salts, e.g., dialkyldimethyl and alkyltrimethyl ammonium salts, alkylbenzyldimethyl ammonium chlorides, and alkylpyridinium halides. Amphoteric surfactants are known in the art and include alkylbetaines, amidopropylbetaines and imidazolinium derivatives. In various embodiments, other materials such as, for example, nucleic acids, for example RNA, single strand DNA and double strand DNA.

The term "complexing agent" as used herein refers to a substance capable of forming a complex compound with another material in solution. Suitable complexing agents can include chelates, ligands and the coatings referred to above. In various embodiments, the complexing agent acts as a label. For example, the complexing agent can include any material capable of functioning as a label, and can include dyes, phosphor particles, and fluorescent dots. In various embodiments, a substance to be separated can be solubilized with a dye-labeled, phosphor-labeled, or quantum dot-labeled material such as a polyelectrolyte, starch, or nucleic acid, for example single-strand DNA.

The complexing agent can include a dye, for example a fluorescent dye. Examples of fluorescent dyes include fluorescein, 6-carboxyfluorescein, 2',4',5',7',-tetrachloro-4,7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX). Fluorescent dyes are described in, e.g., U.S. Pat. No. 4,855,225; Menchen et al, U.S. Pat. No. 5,188,934; and Haugland, R. P., Handbook of Fluorescent Probe and Research Chemicals, 6th edition (1996). The complexing agent can also be chosen from phosphor particles and quantum dots. In various embodiments, the complexing agent can form reversible or irreversible complexes with the substance in solution.

The complexing agent can include phosphor particles. The phosphor can contain zinc sulfide-based electroluminescent materials. Such phosphors are well-known and commonly include one or more of such compounds as copper sulfide (CuS), zinc selenide (ZnSe), and cadmium sulfide (CdS) in solid solution within the zinc sulfide crystal structure, or as second phases or domains within the particle structure. Phosphors commonly contain moderate amounts of other materials such as dopants, e.g., bromine, chlorine, manganese, silver, etc., as color centers, as activators, or to modify defects in the particle lattice to modify properties of the phosphor as desired. Commercially available phosphors include Sylvania Type 723, 728, and 830 Phosphors. The phosphor particles used herein may be of many sizes, having average particle diameters of between about 1 and about 50 microns, such as from about 10 to about 40 microns.

The term "quantum dots" as used herein refers to semiconductor nanocrystals with size-dependent optical and electronic properties. When quantum dots are illuminated with a primary energy source, a secondary emission of energy occurs of a frequency that corresponds to the band gap of the semiconductor material used in the quantum dot. Thus, quantum dots are capable of fluorescence when excited by light. The use of quantum dots as labels in biological applications is disclosed in U.S. Pat. No. 6,855,551.

The term "separation medium" as used herein refers to any medium capable of separating one substance from another based on at least one physical property. For example, the separation medium can separate substances based on at least one of size, affinity for the separation medium, and dielectric constant. In various embodiments, suitable separation media can be chosen from those used in capillary electrophoresis. Suitable non-limiting examples of separation media include water, aqueous buffer solutions, solutions of water-soluble sieving polymers, hydrated crosslinked hydrogels, including physically crosslinked hydrogels, and combinations thereof. Water-soluble sieving polymers include hydroxyethylcellulose, polyethylene oxide, polyacrylamide and poly(N,N-dimethylacrylamide). Suitable hydrated crosslinked hydrogels include agar and agarose gel. Chemically (covalently) crosslinked hydrogels include poly and copoly(N-vinylamide)s as disclosed in U.S. Patent Application Publication 2005/0025741 (the disclosure of which is incorporated by reference herein). In various embodiments, the separation medium can be a porous material, for example, a porous polymer monolith (Stchowiak et al., *Electrophoresis* 2003, 24, 3689-3693; Rohr et al., *Macromolecules* 2003, 36, 1677-1684), or porous polymer beads, for example polystyrene beads, permeated or swollen with a mobile phase. The porous material can be hydrophobic or hydrophilic. The separation media can be chosen to separate substances on the basis of size, affinity for the separation medium, and/or dielectric constant. The selection of mobile phases useful for, e.g., size-based separation can be based on the principles of gel permeation chromatography.

Reference will now be made to various exemplary embodiments, examples of which are illustrated in the accompanying drawings. Wherever possible, the same reference numbers are used in the drawings and the description to refer to the same or like parts.

In various embodiments, and as illustrated in FIG. 2, a system for separating substances comprises a chamber 10 for substances 100, and can include a circuit around liquid sample layer 20. Chamber 10 can be a microchannel, for example a capillary, disposed on a microchip. Substances 100 are disposed within separation medium 15. The system can include transparent substrates 30 and 35 to generally form a liquid sample cavity for liquid sample layer 20. A first side of the liquid sample cavity is formed from a transparent substrate 30 with a transparent electrode 50, and the second side is formed by a transparent substrate 35 and an electrode 60. In various embodiments, the substrate 35 adjacent to electrode 60 can be non-transparent and constructed of any material that can withstand the processing conditions for deposition of the photoconductive material.

The transparent electrode 50 and electrode 60 are electrically coupled to power supply 40. In various embodiments, the transparent electrode 50 can be gold or ITO, the power supply can be AC or DC, and the electrode 60 can be a thin aluminum electrode. The electrodes do not have to be the same. One of the electrodes can be configured as an array of individually controlled electrodes capable of providing a traveling wave to manipulate biological material. In various embodiments, the AC current can have a high frequency ranging from 1 kHz to 10 MHz. In various embodiments, the AC current can have a low frequency ranging from less than 10 Hz to less than 1 kHz. In various embodiments, the applied AC or DC electric field can be high, ranging from 100 volts to 100 kilovolts. In various embodiments, the applied AC or DC electric field can be low, ranging from 1 to 100 volts.

The circuit in FIG. 2 is closed by photoconductive material 70, and is shown in its dark state. In various embodiments, the photoconductive material 70 can be separated from the liquid sample layer 20 by a transparent material 80. Similarly, transparent electrode 50 can be separated from liquid sample layer 20 by transparent material 90. Transparent materials 80 and 90 can function as surface modifier layers capable of reducing non-specific adsorption of substances such as biomolecules. Materials 80 and 90 can be the same or different and can be chosen from, for example, a polymer dielectric, an insulating SOG, a semiconductive SOG, a semiconductive transparent film, or a silicon nitride film. In various embodiments, transparent materials 80 and 90 can be hydrophilic polymer layers. Examples of suitable polymers include hydrophilic polymers, i.e., polymers having hydrophilic moieties, for example poly(ethylene glycol), polyethylene oxide (PEO), and polyacrylamides and copolymers thereof. In various embodiments, the polymers are grafted onto the respective supports 50 and 70. Suitable surface modifiers and methods for modifying surfaces are disclosed in U.S. patent Ser. No. 10/979,645 (filed Nov. 1, 2004), the disclosure of which is incorporated herein by reference in its entirety.

In various embodiments, transparent electrode 50 is a transparent layer of gold, 70 to 80 Å thick, vapor-deposited on substrate 30. In various embodiments, substrate 30 is glass that has been surface treated by, for example, mercaptopropylmethyldimethoxysilane (Gelest, Inc., Tullytown, Pa.). Transparent material 90 is a thin layer, for example a monolayer, of PEO deposited by exposing electrode 50 to a solution of mercapto-PEO, for example methoxypoly(ethyleneglycol) thiol (Nektar, Inc., Hunstville, Ala.). Similarly, and according to various embodiments, transparent material 80 can be an equivalent monolayer of PEO deposited on photoconductive material (e.g., amorphous silica) 70 with a PEO-silane agent, for example, 2-[methoxy(polyethyleneoxy)propyl]trimethoxysilane (Gelest, Inc., Tullytown, Pa.).

Figure 3C:
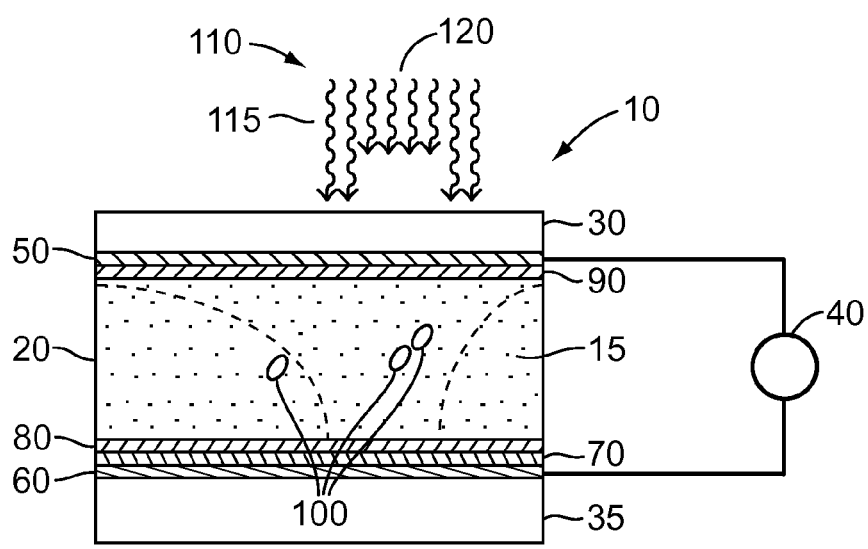

FIGS. 3A-3C illustrate the separation of particles by negative DEP forces. FIG. 3A illustrates an optically activated chamber 10, a portion of which is illuminated by light 110. The light 110 can be focused to illuminate a portion of photoconductive material 70, thereby closing the circuit between transparent electrode 50 and electrode 60. The closed circuit can generate a non-uniform electric field between the activated portion of the photoconductive material 70 and the transparent electrode 50 on the opposite side.

The lines representing light 110 are drawn in various lengths to demonstrate the patterned intensity of the light. The outer edges of the directed light are shown as having a higher intensity than the center of the directed light. The varying degrees of intensity for the light can be provided by means of lenses, mirrors, filters and other means known to those of ordinary skill in the art of optics. For example, and as illustrated in FIG. 3B, the light can take the form of a light cage focused in a ring-shaped pattern. The light has a greater intensity at the outer edge (115) of the ring, resulting in a higher electric field strength compared to the inside of the ring (120). The light forms a "cage" around the particles by taking advantage of the fact that negative DEP forces repel particles 100 away from the high field region.

According to various embodiments, multiple particles in the chamber can be gathered into a light cage by gradually focusing the light to a narrower field. As the field narrows, the particles will be trapped in the electric field minimum in the center of the cage. When the light cage moves, as in FIG. 3C, the particles move in the same direction as the light but with a position offset from the center of the cage so that the DEP forces move the particle towards the center of the cage. As the light cage moves the particles through the separation medium 15, the balance between the DEP forces and the viscosity forces can be disrupted. As a result, some of the particles may escape from the cage and remain entrained in the separation medium, thereby resulting in particle separation.

Figure 4A:
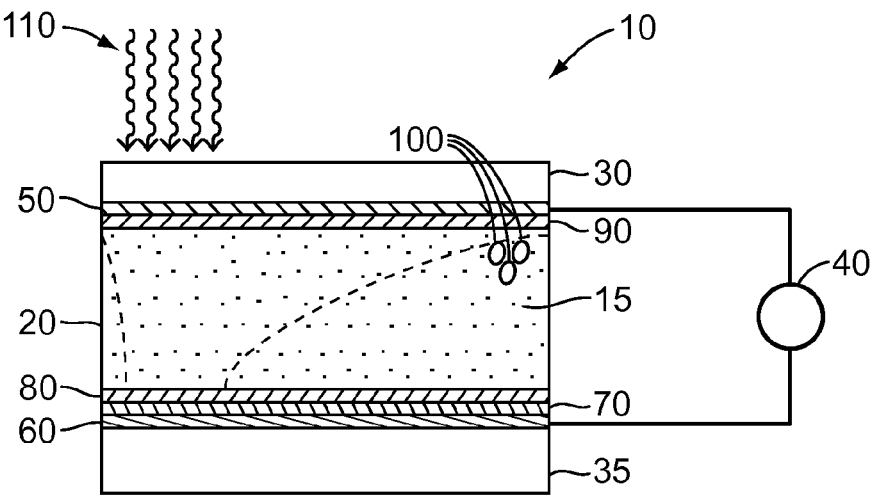
FIGS. 4A-4B illustrate a process for separating substances using negative DEP force according to the present teachings.
Figure 4B:
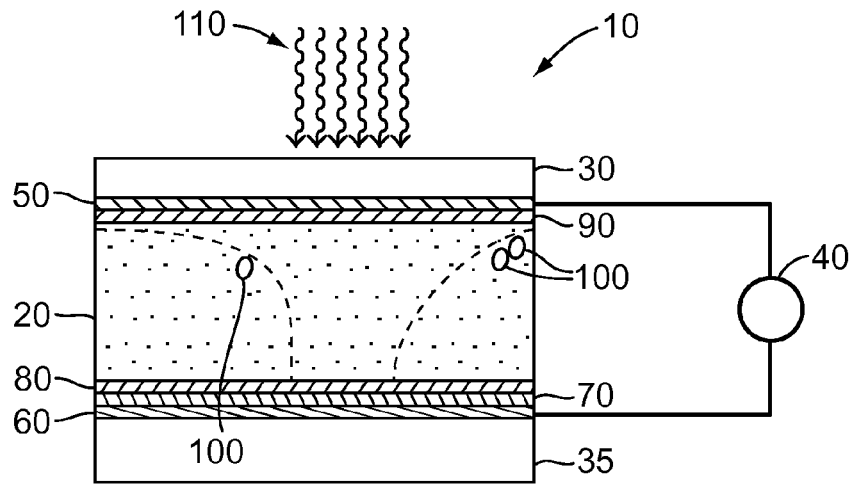

FIGS. 4A-4B illustrate another way in which particles can be separated by negative DEP without using a light cage. This embodiment uses the leading edge of a moving beam of directed light to push substances through a separation medium. In FIG. 4A, light 100 (of uniform intensity) is focused on photoconductive material 70 at a point lateral to the substances to be separated. As the directed light sweeps along the length of the photoconductive material and towards the substances, the substances move in the direction of the lower electric field region. As illustrated in FIG. 4B, the substances may be separated when the dielectric forces fail to move at least a portion of the substances through the separation medium.

Figure 5A:
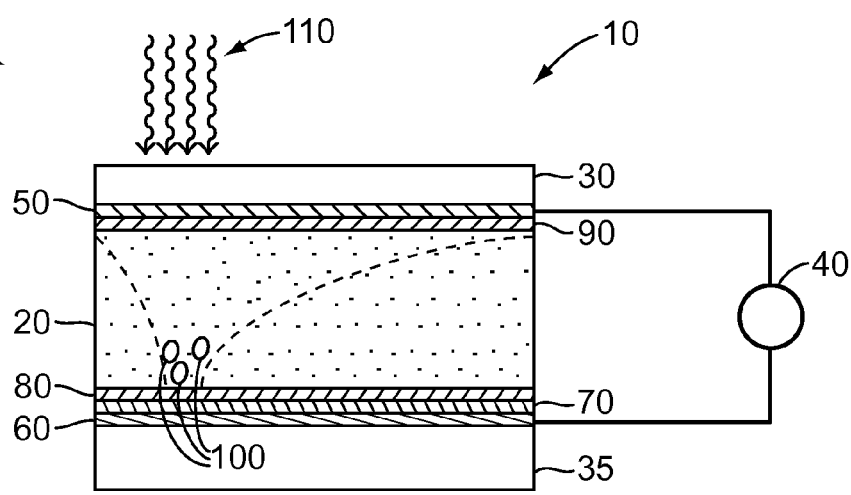
FIGS. 5A-5B illustrate a process for separating substances using positive DEP force according to the present teachings.
Figure 5B:
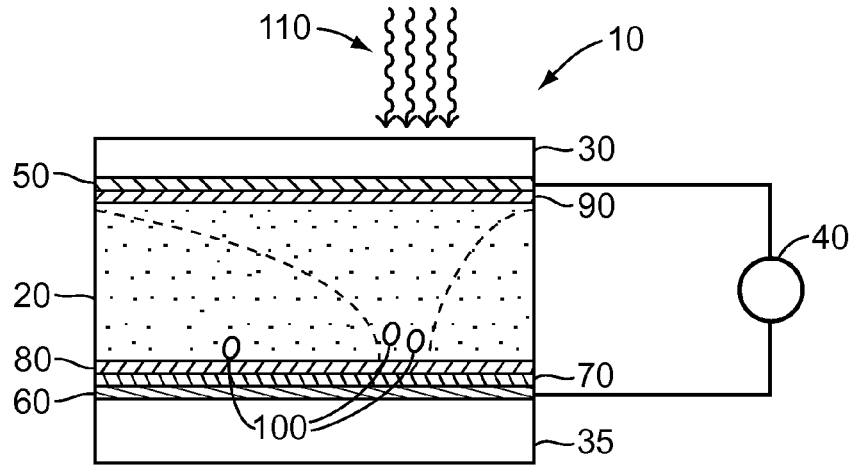

FIGS. 5A-5B illustrate particle separation using positive DEP. Positive separation of substances results when the Clausius-Mositti factor has a positive value, resulting in the movement of the substances toward a higher electric field region (as opposed to a lower one as in negative DEP). Before light 100 is turned on, the electric field in the liquid sample is very weak, and the particles are randomly distributed. When light 100 is focused to illuminate a portion of photoconductive material 70, as illustrated in FIG. 5A, the particles start to move towards the light and are eventually gathered at the focal spot. The particles are then trapped over the surface of photoconductive material 70 due to the electric field gradient in the vertical direction. Unlike the negative DEP regime illustrated above, the edges and center of the directed light can be of uniform intensity.

In FIG. 5B, the directed light moves laterally with respect to the liquid sample chamber 20. The balance between dielectrophoretic and other forces can be disrupted, and at least a portion of the substances can become entrained in the separation medium. This results in separation of the particles.

In various embodiments, the chamber for manipulation with optical activation can be incorporated as an integral part of an optical microscope. The chamber for manipulation can be an integral part of an optical microscope for sorting substances, for example labeled substances. The chamber for manipulation of the substances could use the illumination source of the microscope and focus the light according to the present teachings. This could be done with conventional and confocal type of microscopes. The focusing lens of the microscope optics can be used to focus the light.

In various embodiments, the process is automated. For example, in the case of using negative DEP forces to separate carbon nanotubes, a light cage is created via a software package coupled to an optics system. The light cage is automated, and provides a continuous sorting and manipulation process with a feedback mechanism. The carbon nanotubes can be solubilized with a dye-labeled, quantum-dot labeled, or phosphor-labeled surface-active agent such as a starch, polyelectrolyte, or nucleic acid. This enables visualization to be a part of the automated process.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a surface active agent" includes two or more different surface active agents. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A process for separating substances in a liquid sample cavity containing a separation medium, the process comprising:
    positioning an electrode adjacent to a photoconductive material, wherein the liquid sample cavity comprises a first surface and a second surface, a transparent electrode is positioned proximate to the first surface, and the photoconductive material is positioned proximate to the second surface; and
    illuminating a portion of the photoconductive material with light to close a circuit between the electrode and the transparent electrode to generate an electric field sufficient to move at least one substance across at least a portion of said separation medium, wherein the separation medium separates the substances by differences in dielectric constant between the substances and the medium.

2. The process according to claim 1, wherein the light is moveably directed across the photoconductive material.

3. The process according to claim 1, wherein said liquid sample cavity is a microchannel.

4. The process according to claim 3, wherein the microchannel is disposed on a microchip.

5. The process according to claim 1, wherein the substances are chosen from DNA, RNA, lipids, terpenes, proteins, polysaccharides, and carbon nanotubes.

6. The process according to claim 1, wherein the substances are chosen from semiconducting carbon nanotubes and metallic carbon nanotubes.

7. The process according to claim 1, wherein the surface of at least one of the substances comprises at least one surface active agent.

8. The process according to claim 7, wherein the at least one surface active agent is chosen from non-ionic surfactants, anionic surfactants, and cationic surfactants.

9. The process according to claim 1, wherein the substances are labeled with at least one complexing agent chosen from fluorescent dyes, phosphor particles, and quantum dots.

10. The process according to claim 9, wherein the substances are reversibly complexed to a labeled complexing agent.

11. The process according to claim 1, wherein an electric field between the transparent electrode and the electrode provides dielectrophoretic manipulation to at least one of said substances.

12. The process according to claim 1, wherein the separation medium is chosen from water, aqueous buffer solutions, water-soluble polymers, hydrated crosslinked hydrogels, hydrophilic porous polymer monoliths, and combinations thereof.

13. The process according to claim 1, wherein the separation medium is a hydrophilic porous polymer monolith filled with another medium chosen from water, aqueous buffer solutions, water-soluble polymers, hydrated crosslinked hydrogels, and combinations thereof.

14. The process according to claim 1, wherein the separation medium separates the substances by size.

15. The process according to claim 1, wherein the separation medium separates the substances by its affinity to the separation medium.

16. The process according to claim 1, further comprising generating an image of at least one of the substances.

17. The process according to claim 16, wherein the image is generated with a microscope and a camera.

18. The process according to claim 17, wherein the microscope is a fluorescent microscope, and the camera is a digital camera.

19. A process for separating substances comprising:
    contacting a separation medium with said substances to form a composition;
    disposing said composition in a liquid sample cavity comprising a first surface and a second surface, wherein:
    a transparent electrode is positioned proximate to the first surface;
    a photoconductive material is positioned proximate to the second surface; and
    an electrode is positioned adjacent to the photoconductive material; and
    illuminating a portion of the photoconductive material with light to close a circuit between the electrode and the transparent electrode to generate an electric field sufficient to move at least one substance across at least a portion of said separation medium, wherein the separation medium separates the substances by differences in dielectric constant between the substances and the medium.

20. The process according to claim 19, wherein said liquid sample cavity is a microchannel.

21. The process according to claim 19, wherein the microchannel is disposed on a microchip.

22. The process according to claim 19, wherein the substances are chosen from DNA, RNA, lipids, terpenes, proteins, polysaccharides, and carbon nanotubes.

23. The process according to claim 19, wherein the substances are chosen from semiconducting carbon nanotubes and metallic carbon nanotubes.

24. The process according to claim 19, wherein the surface of at least one of the substances comprises at least one surface active agent.

25. The process according to claim 24, wherein the at least one surface active agent is chosen from non-ionic surfactants, anionic surfactants, and cationic surfactants.

26. The process according to claim 19, wherein the substances are labeled with at least one complexing agent chosen from fluorescent dyes, phosphor particles, and quantum dots.

27. The process according to claim 26, wherein the substances are reversibly complexed to a labeled complexing agent.

28. The process according to claim 19, wherein an electric field between the transparent electrode and the electrode provides dielectrophoretic manipulation at least one of said substances.

29. The process according to claim 19, wherein the transparent electrode comprises gold.

30. The process according to claim 19, wherein the separation medium is chosen from water, aqueous buffer solutions, water-soluble polymers, hydrated crosslinked hydrogels, hydrophilic porous polymer monoliths, and combinations thereof.

31. The process according to claim 19, wherein the separation medium is a hydrophilic porous polymer monolith filled with another medium chosen from water, aqueous buffer solutions, hydrated crosslinked hydrogels, and combinations thereof.

32. The process according to claim 19, wherein the separation medium separates the substances by size.

33. The process according to claim 19, wherein the separation medium separates the substances by their affinity to the separation medium.

34. The process according to claim 19, further comprising generating an image of at least one of the substances.

35. The process according to claim 34, wherein the image is generated with a microscope and a camera.

36. The process according to claim 35, wherein the microscope is a fluorescent microscope, and the camera is a digital camera.

37. A process for separating carbon nanotubes comprising:
   disposing the carbon nanotubes and a liquid separation medium in a liquid sample cavity wherein:
   the liquid sample cavity comprises a first surface and a second surface;
   a transparent electrode is positioned proximate to the first surface;
   a photoconductive material is positioned proximate to the second surface; and
   an electrode is positioned adjacent to the photoconductive material; and
   illuminating a portion of the photoconductive material with light to close a circuit between the electrode and the transparent electrode to generate an electric field sufficient to move at least one carbon nanotube across at least a portion of said separation medium, wherein the separation medium separates the carbon nanotubes by differences in dielectric constant between the at least one carbon nanotube and the medium.

38. The process according to claim 37, wherein the carbon nanotubes are single-wall nanotubes.

39. The process according to claim 37, wherein the carbon nanotubes are single-wall carbon nanotubes chosen from semiconducting carbon nanotubes and metallic carbon nanotubes.

40. The process according to claim 37, wherein the surface of the carbon nanotubes comprises at least one surface active agent.

41. The process according to claim 40, wherein the at least one surface active agent is chosen from non-ionic surfactants, anionic surfactants, and cationic surfactants.

42. The process according to claim 37, wherein the light is moveably directed across the photoconductive material.

43. The process according to claim 37, wherein said liquid sample cavity is a microchannel.

44. The process according to claim 43, wherein the microchannel is disposed on a microchip.

45. The process according to claim 37, wherein the carbon nanotubes are labeled with at least one complexing agent chosen from fluorescent dyes, phosphor particles, and quantum dots.

46. The process according to claim 45, wherein the carbon nanotubes are reversibly complexed to a labeled complexing agent.

47. The process according to claim 37, wherein an electric field between the transparent electrode and the electrode provides dielectrophoretic manipulation to carbon nanotubes.

48. The process according to claim 37, wherein the separation medium is chosen from water, aqueous buffer solutions, water-soluble polymers, hydrated crosslinked hydrogels, hydrophilic porous polymer monoliths, and combinations thereof.

49. The process according to claim 37, wherein the separation medium is a hydrophilic porous polymer monolith filled with another medium chosen from water, aqueous buffer solutions, hydrated crosslinked hydrogels, and combinations thereof.

50. The process according to claim 37, wherein the separation medium separates the carbon nanotubes by size.

51. The process according to claim 37, wherein the separation medium separates the carbon nanotubes by the affinity of at least one of the carbon nanotubes to the separation medium.

52. The process according to claim 37, further comprising generating an image of at least one of the carbon nanotubes.

53. The process according to claim 52, wherein the image is generated with a microscope and a camera.

54. The process according to claim 53, wherein the microscope is a fluorescent microscope, and the camera is a digital camera.

55. The process according to claim 54, wherein the microscope is a fluorescent microscope, and the camera is a digital camera.

* * * * *